United States Patent [19]
Coates et al.

[11] Patent Number: 5,996,579
[45] Date of Patent: *Dec. 7, 1999

[54] BAG-VALVE-MASK RESUSCITATOR ATTACHMENT

[76] Inventors: Michael R. Coates; Donna F. Coates, both of 5404 - 80th Ave. Cir. E, Palmetto, Fla. 34221

[ * ] Notice: This patent is subject to a terminal disclaimer.

[21] Appl. No.: 09/105,109

[22] Filed: Jun. 26, 1998

[51] Int. Cl.⁶ .............................. A62B 9/04; A61M 16/10
[52] U.S. Cl. ................ 128/205.13; 128/202.27; 128/203.12; 128/207.16; 128/205.17
[58] Field of Search ........................ 128/202.28, 203.12, 128/205.13, 205.14, 205.15, 205.16, 205.17, 205.26, 205.24, 204.18, 207.15, 207.16, 203.28, 202.27

[56] References Cited

U.S. PATENT DOCUMENTS

| | | | |
|---|---|---|---|
| 4,953,547 | 9/1990 | Poole, Jr. | 128/203.12 |
| 5,181,508 | 1/1993 | Poole, Jr. | 128/203.12 |
| 5,329,921 | 7/1994 | Socaris et al. | 128/203.12 |
| 5,359,998 | 11/1994 | Lloyd | 128/203.11 |
| 5,443,059 | 8/1995 | Kock et al. | 128/203.12 |
| 5,485,835 | 1/1996 | Vande Streek et al. | 128/205.13 |
| 5,613,489 | 3/1997 | Miller et al. | 128/203.28 |
| 5,617,844 | 4/1997 | King | 128/200.18 |
| 5,701,886 | 12/1997 | Ryatt | 128/203.12 |
| 5,749,358 | 5/1998 | Good et al. | 128/205.23 |
| 5,762,063 | 6/1998 | Coates et al. | 128/205.13 |
| 5,763,792 | 6/1998 | Kullik | 73/861.52 |
| 5,791,340 | 8/1998 | Schleufe et al. | 128/203.12 |
| 5,842,467 | 12/1998 | Greco | 128/205.13 |

*Primary Examiner*—John G. Weiss
*Assistant Examiner*—Todd Martin
*Attorney, Agent, or Firm*—Dorothy S. Morse

[57] ABSTRACT

An improved medication introducing device for airtight connection between a bag-valve mask resuscitator apparatus, or other similar pre-hospital emergency respiratory device, and an endo-tracheal tube installed in a patient, the device comprising a central housing having a top opening, a bottom opening, and a minimum of two medication administering ports, at least one of the ports being an injection port for emergency administering of medications through pre-filled syringes into patients for which an intravenous line cannot be established, medications such as cardiac medications including atropine, epinephrine, lidocaine, and narcan, and at least one port being a nebulizer port for administering asthma medications to an intubated patient undergoing pre-hospital emergency, and where the improvement comprises one or more back flow reducing means to maximize the flow of administered nebulized medications to the patient. It is contemplated for the present invention to be made from chemically inert materials, to have a sufficiently low manufacturing cost so that it can be disposable, and for each port to have an airtight end cap. Applications may include, but are not limited to, pre-hospital emergency and rescue situations in which a bag-valve mask apparatus must be used to perform CPR on an intubated patient.

20 Claims, 2 Drawing Sheets

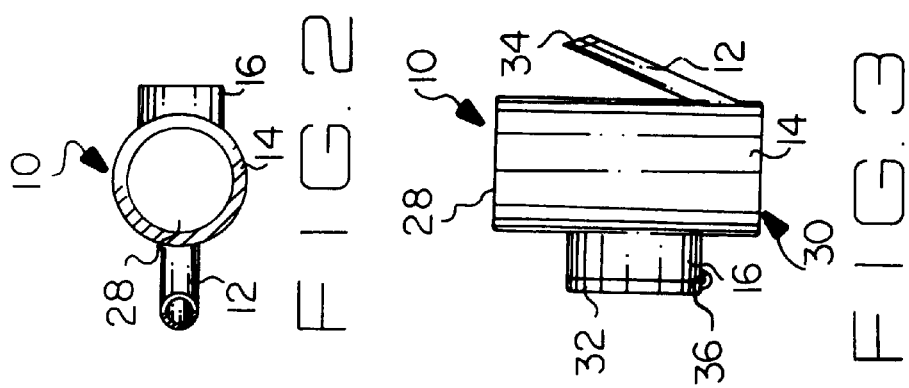
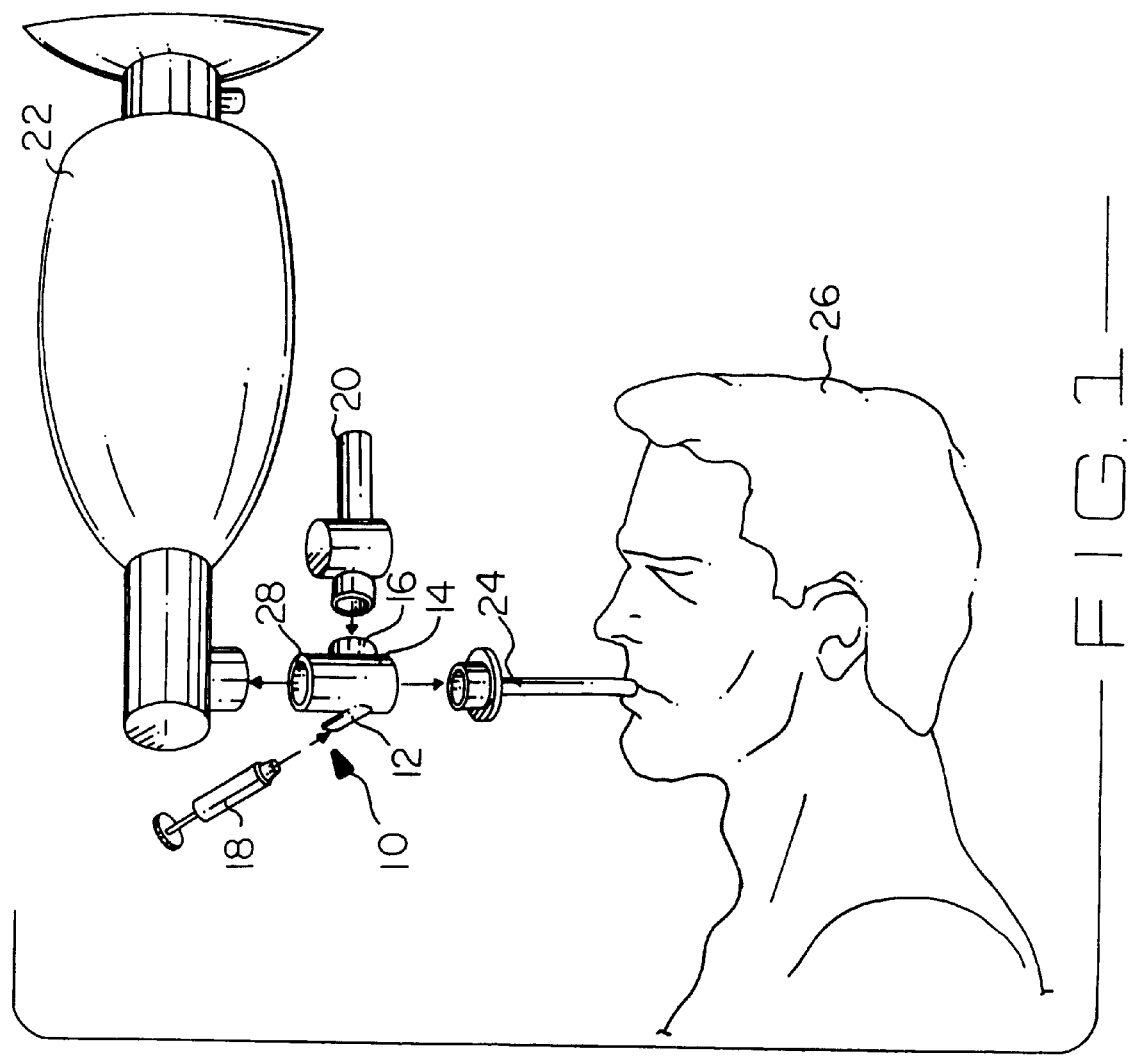

BAG-VALVE-MASK RESUSCITATOR ATTACHMENT

BACKGROUND—FIELD OF INVENTION

The preferred embodiments of the device herein disclose improvements for the invention disclosed by the above-named inventors in U.S. Pat. No. 5,762,063 (1998). This invention relates to adapters and other devices for use with pre-hospital respiratory assist equipment, specifically to a device for use with the type of bag-valve mask apparatus commonly used for pre-hospital emergency respiratory assistance when CPR must be given to an intubated patient, the device comprising a central housing having an upper opening dimensioned for airtight connection to the bag-valve mask apparatus, a lower opening dimensioned for airtight connection to the endo-tracheal tube, and a minimum of two laterally positioned ports therethrough, at least one port being a syringe injection port for the emergency administering of medications, such as cardiac medications, into patients for whom intravenous injection cannot be established, and at least one port being a nebulizer port for administering asthma medications to intubated patients while they are undergoing CPR, wherein the improvements comprise changes in the configuration of the nebulizer port and optional changes in its end cap which would maximize the amount of administered nebulized medication reaching the patient. Applications may include, but are not limited to, emergency and rescue situations in which a bag-valve mask apparatus is used on an intubated patient so that CPR won't have to be interrupted to administer medications to such patients.

BACKGROUND—DESCRIPTION OF PRIOR ART

In emergency and rescue situations which necessitate cardiac pulmonary resuscitation (CPR), it is common for patients to require medications, such as cardiac medications, and for such medications to be administered through the use of an intravenous line. However, establishing an intravenous line can be difficult and time consuming in some patients. For example, this can be due to the type of injury sustained by the patient, obesity, diabetes, as well as many other factors. When an intravenous line cannot be attempted or the establishment of an intravenous line has been attempted and failed, emergency medical personnel must look for alternative ways in which to administer the medications indicated by the patient's condition.

A secondary approved method for administering medications to a patient can be performed through the trachea which allows the medications to be absorbed into the bloodstream through the lungs. By using a syringe, medications are injected into an endo-tracheal tube which is placed through the mouth and connects with the patient's trachea. However, when the type of bag-valve mask apparatus commonly used for pre-hospital CPR is connected to the endo-tracheal tube, CPR must be interrupted to administer the medications to the patient by this secondary method at a risk to the patient.

When encountering a patient requiring CPR in a pre-hospital situation, one of the first things that emergency medical personnel are known to do is to intubate the patient by placing a plastic tube into the patient's trachea. The endo-tracheal tube maintains the trachea in an open condition and provides a conduit for administering medications. However, prior to injecting medications into the tube through pre-filled syringes, and before the Coates invention in U.S. Pat. No. 5,762,063 (1998) mentioned above, CPR was stopped, the bag-valve mask apparatus or other type of pre-hospital artificial respiratory assist device was disconnected from the endo-tracheal tube, and the medication injected into the tube, after which the artificial respiratory assist device was reattached to the endo-tracheal tube before CPR was resumed. Disadvantages of this pre-Coates procedure involved both the risks associated with the interruption of CPR, as well as the risk of dislodging the endo-tracheal tube during the disconnection and reconnection of the artificial respiratory assist device.

In addition, pre-hospital emergency medical personnel also often encounter asthmatic patients who require endo-tracheal intubation and artificial respiration. Prior to the Coates device, such patients had been at an extreme disadvantage since there were no pre-hospital artificial respiration devices then available to rescue workers for providing nebulized asthma medication to them. Again, as with the administering of injected medications, when a bag-valve mask apparatus, or similar pre-hospital respiratory assistance device was used with an intubated patient, the artificial respiratory process was necessarily interrupted at risk to the patient whenever the patient's condition indicated a need for administering nebulized asthma medication. Before the disclosure in U.S. Pat. No. 5,762,063 to Coates (1998), it was not known to have a device for use with the type of bag-valve mask apparatus commonly used for pre-hospital emergency respiratory assistance during CPR, the device configured for airtight connection between the bag-valve mask apparatus and the upper portion of the endo-tracheal tube inserted into a patient for maintaining the trachea in an open position, and comprising a central housing having an upper opening dimensioned for connection to the bag-valve mask apparatus, a lower opening dimensioned for connection to the endo-tracheal tube, and a minimum of two ports laterally positioned through the central housing, at least one of the ports being a syringe injection port for the emergency administering of medications into patients for whom intravenous lines could not be established, such as for administering cardiac medications including atropine, epinephrine, lidocaine, and narcan to a patient during CPR, and at least one nebulizer port for administering asthma medications during CPR so that the bag-valve mask apparatus does not have to be disconnected from the endo-tracheal tube and CPR thereby discontinued during the administering of such medications during pre-hospital emergency care.

While U.S. Pat. No. 5,762,063 to Coates (1998) discloses a simple, compact, lightweight, and disposable device with at least two medication introducing ports therethrough which could be made readily available to emergency medical personnel in pre-hospital rescue situations so that they can more quickly adapt to the changing needs of patients, after the administering of nebulized medication and when the bag-valve mask is next activated during the continuation of CPR to force air into the patient, a small amount of the administered nebulized medication might be forced back through the nebulizer port since the nebulizers typically used by emergency medical personnel are open-ended. To maximize the amount of nebulized medication reaching the patient, the present invention discloses varying combinations of nebulizer port configuration changes, deflective barriers, and changes in the configuration of the nebulizer port cap.

SUMMARY OF INVENTION—OBJECTS AND ADVANTAGES

It is the primary object of this invention to provide a means of administering medications by both injection and nebulization into an endo-tracheal tube positioned in the trachea of a patient undergoing CPR and whose endo-tracheal tube is connected to a bag-valve mask apparatus, or other similar pre-hospital emergency respiratory assistance device, so that the medication can move through the lungs and into the bloodstream without disconnection of the bag-valve mask apparatus and concomitant interruption of CPR, and wherein the administering means maximizes the amount of nebulized medications reaching the patient. It is also an object of this invention to provide a means for pre-hospital emergency personnel to administer both cardiac medications, such as Atropine, Epinephrine, Lidocaine, and Narcan, and asthma medications, such as Proventil, and Isoetherine, to patients who require intubation without interruption of CPR. A further object of this invention is to provide a medication introducing device for use between a bag-valve mask apparatus and an endo-tracheal tube which is compact in size, and easy to connect between a bag-valve mask apparatus and an endo-tracheal tube for rapid installation and quick initiation of CPR. It is also an object of this invention to provide a medication introducing device for use between a bag-valve mask apparatus and an endo-tracheal tube which is made from materials that are chemically inert. A further object of this invention is to provide a medication introducing device which has airtight sealing means for connection to its medication introducing ports, and for which the nebulizer port sealing means is also configured for optional attachment to one or both of the openings in the nebulizer connected to the nebulizer port. It is also an object of this invention to provide a medication introducing device for use between a bag-valve mask apparatus and an endo-tracheal tube which is sufficiently low in cost to be disposable.

As described herein, properly manufactured and connected between a bag-valve mask device, or similar pre-hospital emergency respiratory assistance device, and an endo-tracheal tube installed within a patient for maintaining the patient's trachea in an open position during emergency treatment, the present invention would provide pre-hospital emergency medical personnel with a means of administering injected and nebulized medications to the patient without the interruption of CPR. Since intravenous lines cannot be established in many patients for the emergency administering of medications, alternative delivery means for such medications is required. The present invention provides a disposable, compact, easily handled, and inexpensively manufactured medication introducing device for administering of medication through the trachea, which is a secondary approved method for delivery of some medications. The present invention would comprise a central housing with a top opening configured for connection to the air exhaust tube of a pre-hospital bag-valve mask device, a bottom opening for connection to the upper portion of an endo-tracheal tube, and at least two ports laterally positioned through the central housing which communicate with the upper opening in the endo-tracheal tube. At least one port would be configured for injection of medications through pre-filled syringes, and at least one additional port would be configured for connection to the standard size of discharge opening commonly used in nebulizers for administering a fine mist of medication which can be rapidly absorbed into the respiratory tissue of asthma patients. It is contemplated for the housing and ports to be made from chemically inert materials and for each port to have an airtight end cap which can be tightly attached to it to seal it during CPR both before and after medication introduction into a patient. It is also contemplated for the present invention to be compact in configuration with the length of its ports sufficiently long for easy access thereto, but not excessively long that they become cumbersome and interfere with other emergency care procedures. The improvement comprising the present invention addresses the possible occurrence of back flow of small amounts of nebulized medications through the nebulizer port upon each activation of the bag-valve mask during continued CPR. To maximize the amount of nebulized medication reaching the patient, the present invention discloses a nebulizer port having varying combinations of a reduced proximal end, a medication deflecting barrier or shield placed adjacent to the proximal end, and an end cap for the nebulizer port which has a configuration that securely fits over both the nebulizer port opening and at least one of the openings in the open-ended nebulizer.

The description herein provides preferred embodiments of the present invention but should not be construed as limiting the scope of the respiratory assist device invention. For example, variations in the length of the central housing, the materials from which the central housing is made, the lengths of the deflective barriers, the thickness of the material from which the deflective barriers are made, the longitudinal dimension of the injection port and the nebulizer port, the materials from which the end caps are made, and the sealing means by which the end caps are attached to the ports, other than those shown and described herein, may be incorporated into the present invention. Thus the scope of the present invention should be determined by the appended claims and their legal equivalents, rather than the examples given.

BRIEF DESCRIPTION OF THE DRAWINGS

FIG. 1 is an exploded side view of the invention positioned for attachment between a bag-valve mask device and an endo-tracheal tube installed in a patient, and having a syringe and a nebulizer poised for administering medications into an injection port and a nebulizer port, respectively.

FIG. 2 is a top view of the invention having a nebulizer port and injection port laterally depending from opposed sides of a central housing.

FIG. 3 is a side view of the invention with a nebulizer port having a large end cap attached thereto and an injection port in an opposed position from the nebulizer port having a small end cap attached thereto.

DETAILED DESCRIPTION OF PREFERRED EMBODIMENTS

Figure 4A:
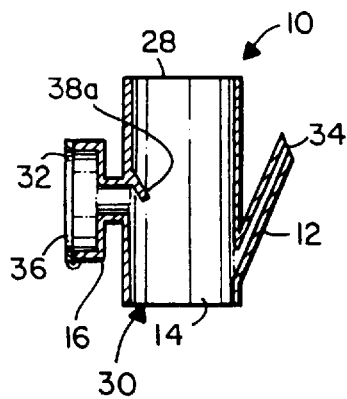
FIG. 4a is a side cross-sectional view of a first embodiment of the nebulizer port of the invention having a reduced proximal end and a rigid downwardly angled deflecting barrier with a planar configuration that is connected to the inside central housing wall adjacent to and above the proximal end.

FIG. 1 shows a preferred embodiment of a bag-valve-mask resuscitator attachment 10 having a central housing 14, with a top opening 28 and a bottom opening, shown in FIG. 3 as number 30. In addition, FIG. 1 shows resuscitator attachment 10 having an injection port 12 depending laterally from central housing 14, and a nebulizer port 16 also depending laterally from central housing 14 in a position opposed to injection port 12. Although the number of injection ports 12 and nebulizer ports 16, and their placement, are not critical to the present invention, it is contemplated in the preferred embodiment to have one injection port 12 and one nebulizer port 16 placed in opposed positions for maximum convenience during use. FIG. 1 shows nebulizer port 16 being larger in diameter than injection port 12, and nebulizer port 16 being positioned approximately perpendicular in its connection to central housing 14. Although not shown, nebulizer port 16 has a hollow interior which communicates with the interior portion of central housing 14. Similarly, injection port 12 has a hollow interior which communicates with the interior portion of central housing 14. However, in the preferred embodiment it is contemplated for injection port 12 to have a narrower diameter than nebulizer port 16 to reduce the interior surface area available for adherence of medications, and for injection port 12 to be positioned at an oblique angle relative to central housing 14 with its lower end positioned below the lower end of nebulizer port 16 to provide the shortest distance possible for medications to travel to reach endo-tracheal tube 24 and to allow gravity to assist the maximum flow of medications from injection port 12 into patient 26. FIG. 1 also shows pharmacological introducing resuscitator attachment 10 poised for connection between a bag-valve mask device 22 positioned over a prone patient 26, and an endo-tracheal tube 24 upwardly depending from the mouth of patient 26. FIG. 1 also shows a syringe 18 and a nebulizer 20 poised for administering medications through injection port 12 and nebulizer port 16, respectively.

FIG. 2 shows nebulizer port 16 and injection port 12 laterally depending from opposed sides of central housing 14. FIG. 2 also shows top opening 28 contemplated for connection to bag-valve mask device 22. In FIG. 2, injection port 12 is shown to angle upwardly from central housing 14 so that gravity will help medications injected therein to move more rapidly downward into endo-tracheal tube 24 and into the lungs of patient 26. FIG. 3 shows resuscitator attachment 10 having nebulizer port 16 depending from one side of central housing 14 and injection port 12 depending from central housing 14 in a position opposed from the nebulizer port. FIG. 3 also shows nebulizer port 16 having a large end cap 32 attached thereto and injection port 12 having a small end cap 34 attached thereto. It is contemplated for large end cap 32 to attach to nebulizer port 16 and for small end cap 34 to attach to injection port 12 so as to each provide an air tight seal during CPR with the use of bag-valve mask devise 22 both before and after medication (not shown) introduction into patient 26. In the preferred embodiment it is contemplated for large end cap 32 to comprise a tight fitting snap-on cap or a threaded cap which prevents large end cap 32 from being forced off of the end of nebulizer port 16 due to the positive pressure generated by CPR. It is only critical that large end cap 32 be able to be easily removed and replaced by rescue workers for rapid initiation of CPR. In the preferred embodiment it is contemplated for small end cap 34 to comprise a plastic or rubber cap similar to the ports found on intravenous tubing which allow medication to be injected therethrough with a syringe and needle, the hole created thereby self-sealing after the needle is withdrawn to prevent air leakage. In addition, although not critical, it is contemplated for an optional connecting member 36 to be connected between large end cap 32 and nebulizer port 16 to retain end cap 32 close at hand when removed from nebulizer port 16. The materials from which connecting member 36 is made are not critical to the present invention. However, in the preferred embodiment, although not limited to the following, it is contemplated for connecting member 36 to be provided in the form of a plastic strap. Should connecting member 36 be used for an embodiment of the present invention, wherein large end cap 32 is also configured for attachment to one end of nebulizer 20 to seal the open end of nebulizer 20 during continued CPR, then connecting means 36 must have sufficient length to allow large end cap 32 to reach the open end of nebulizer 20. In the alternative, connecting means could be configured to allow easy detachment of large end cap 32 from connecting means 36 whereafter large end cap 32 could be separately used as an airtight seal for nebulizer 20.

Figure 4B:
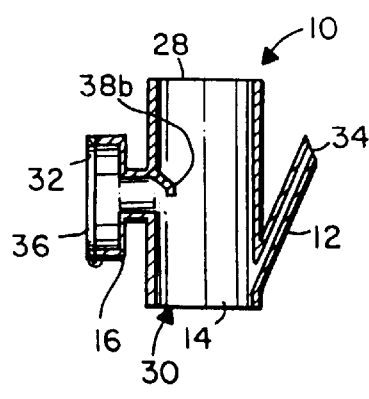
FIG. 4b is a side cross-sectional view of a second embodiment of the nebulizer port of the invention having a reduced proximal end and a rigid downwardly angled deflecting barrier with an end projection bent inwardly therefrom so as to be approximately parallel to the central housing wall, the barrier being connected to the inside central housing wall adjacent to and above the proximal end.
Figure 4C:
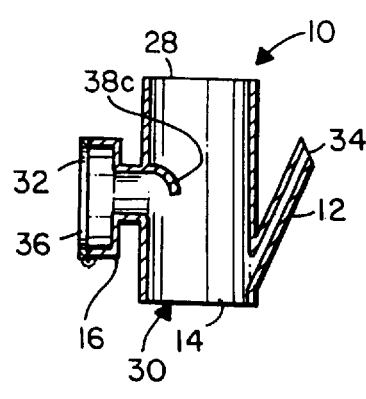
FIG. 4c is a side cross-sectional view of a third embodiment of the nebulizer port of the invention having a reduced proximal end and a rigid downwardly depending arcuate deflecting barrier connected to the inside central housing wall adjacent to and above the proximal end.
Figure 4D:
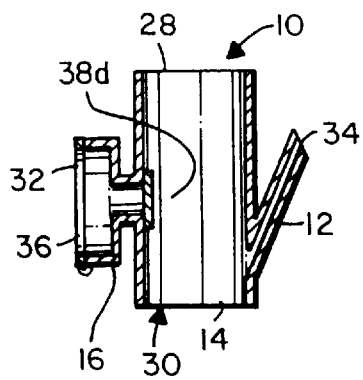
FIG. 4d is a side cross-sectional view of a fourth embodiment of the nebulizer port of the invention having a reduced proximal end and a flexible barrier which covers the proximal end opening during bag-valve mask activation, but which otherwise allows flow of nebulized medication therethrough, the barrier being connected to the inside central housing wall adjacent to and above the proximal end.

FIGS. 4a–4d show several different preferred embodiments of deflecting barriers 38a–38d used to minimize back flow of nebulized medications (not shown) into nebulizer port 16 and maximize flow of nubulized medication into patient 26. FIG. 4a shows a first embodiment of nebulizer port 16 having end cap 32 over its distal end and a reduced proximal end with a rigid downwardly angled planar deflecting barrier 38a connected to the portion of the inside wall of central housing 14 that is adjacent to and above the proximal end of nebulizer port 16. FIG. 4b shows a second embodiment of nebulizer port 16 also having a reduced proximal end and a rigid downwardly angled deflecting barrier 38b connected to the inside central housing wall adjacent to and above the proximal end of nebulizer port 16. In addition, FIG. 4b shows deflecting barrier 38b having an end projection that is bent at an angle relative to the remainder of deflecting barrier 38b so that the end projection is oriented in a position that is approximately parallel to the inside wall of central housing 14. FIG. 4c shows a third embodiment of nebulizer port 16 having a reduced proximal end and a rigid downwardly depending arcuate deflecting barrier 38c connected to the portion of the inside central housing wall adjacent to and above the proximal end of nebulizer port 16. In contrast, FIG. 4d shows a fourth embodiment of nebulizer port 16 having a reduced proximal end and a flexible barrier 38d which covers the proximal end opening of nebulizer port 16 during bag-valve mask activation, but which otherwise is easily separated from the proximal end opening of nebulizer port 16 to allow flow of nebulized medication therethrough. Barrier 38d is also connected to the portion of the inside central housing wall adjacent to and above the proximal end of nebulizer port 16. It is contemplated that rigid barriers 38a–38c be made from the same plastic materials used for central housing 14 and formed as a part the inside wall of central housing 14 through molded construction. The dimensions of barriers 38a–38c are not critical, but none should be so large as to restrict flow of nebulized medications (not shown) into central housing 14 or the flow of air (not shown) from bag-valve mask 22 into intubated patient 26. It is contemplated for flexible barrier 38d to be made from a material having sufficient thickness so that it does not become wrinkled or folded during its movement toward and away from the proximal end opening in nebulizer port 16.

Figure 5A:
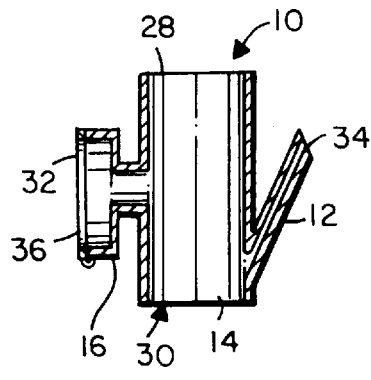
FIG. 5a is a side cross-sectional view of a fifth embodiment of the invention having a nebulizer port comprising two axially aligned and connected cylinders, the smaller cylinder of which creates a reduced diameter proximal end.
Figure 5B:
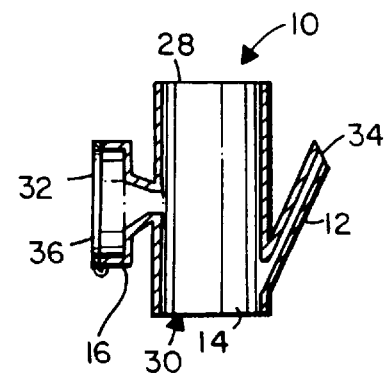
FIG. 5b is a side cross-sectional view of a sixth embodiment of the invention having a nebulizer port with a reduced diameter proximal end, with the larger part of the port being cylindrical and the smaller part tapered therefrom to produce the reduced diameter proximal end.
Figure 5C:
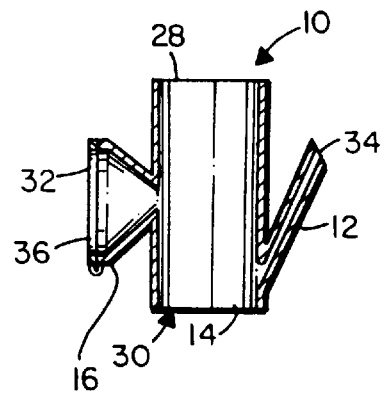
FIG. 5c is a side cross-sectional view of a seventh embodiment of the invention having a nebulizer port with a truncated cone-shaped configuration that creates a reduced diameter proximal end.

FIG. 5a shows a fifth embodiment of resuscitator attachment 10 having a nebulizer port 16 comprising two axially aligned and connected cylinders, the smaller cylinder of which creates a reduced diameter proximal end, while FIG. 5b shows a sixth embodiment having nebulizer port 16 with a reduced proximal end, its larger part being cylindrical in configuration and its smaller part tapering therefrom to produce the reduced diameter proximal end. FIG. 5c provides a seventh embodiment of the present invention having a nebulizer port with a truncated cone-shaped configuration that provides for a reduced diameter proximal end. It is contemplated for the reduced proximal ends of the nebulizer ports 16 shown in FIGS. 5a–5c to reduce the amount of nebulized medication back flow through nebulizer port 16 when bag-valve mask 22 is activated during continued CPR of patient 26, and thereby maximize the amount of nebulized medication reaching patient 26. Although FIGS. 5a–5c show preferred embodiments of several reducing configurations contemplated for nebulizer port 16, the shape of nebulizer port 16 is not critical as long as it is configured to narrow into a reduced dimension proximal end. Therefore, it should be understood that other nebulizer ports 16 having similar configurations are also within the scope of the present invention.

Figure 6A:
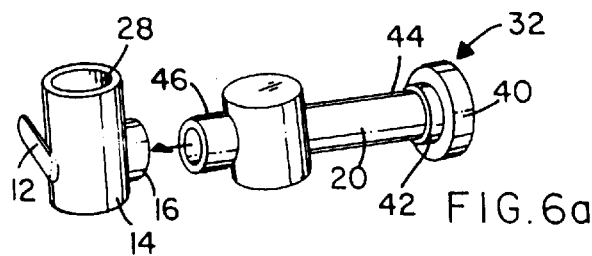
FIG. 6a is a side view of the invention having a two-sided nebulizer port cap, the second side of which is configured for secure temporary attachment to a first end of the open-ended nebulizer, with the cap removed from the nebulizer port and positioned over the first end of the open-ended nebulizer.
Figure 6B:
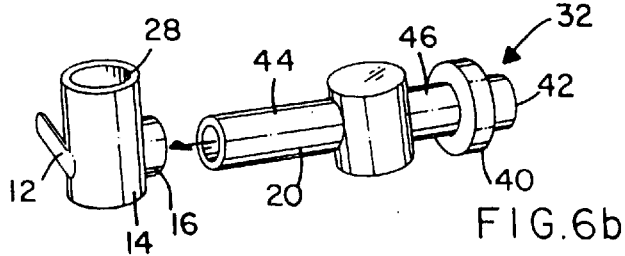
FIG. 6b is a side view of the invention having a two-sided nebulizer port cap, the second side of which is configured for secure temporary attachment to the second end of the open-ended nebulizer with the cap removed from the nebulizer port and positioned over the second end of the open-ended nebulizer.

FIG. 6a shows the present invention having a two-sided nebulizer port cap 32, the first side 40 being configured and dimensioned for secure attachment to the distal end of nebulizer port 16, with the second side 42 being configured and dimensioned for secure attachment to a first end 44 of open-ended nebulizer 20. In FIG. 6a, cap 32 is shown removed from the distal end of nebulizer port 16 and positioned over first end 44 so that during continuation of CPR a maximum amount of nebulized medication will be directed into patient 26 with little or no nebulized medication flowing back through nebulizer port 16. FIG. 6b shows the present invention having a two-sided nebulizer port cap 32, the first side 40 of which is configured and dimensioned for secure attachment to both the distal end of nebulizer port 16 and the second end 46 of open-ended nebulizer 20. In FIG. 6b, it is contemplated for second side 42 of cap 32 to be dimensioned for secure air-tight connection to first end 44. It is also contemplated to have another embodiment wherein nebulizer port 16 is configured and dimensioned intermediate of the dimensions of first end 44 and second end 46, and with cap 32 being made from a flexible or stretchable material so that cap 32 can be securely force-fit over all three openings, to include the opening in the distal end of nebulizer port 16, first end 44, and second end 46. Further, it is contemplated for nebulizer port 16 to be manufactured with a diameter dimension identical to that of either first end 44 or second end 46, so that one single-sided cap 32, as shown in FIGS. 4a–4d and FIGS. 5a–5c, would securely seal both nebulizer port 16 and one end of open-ended nebulizer 20. It is not contemplated for the configuration of cap 32 to be limited to the examples given. It is only critical that the configuration and dimension of cap 32 allow it to securely seal the distal end of nebulizer port 16 and one of the open ends of nebulizer 20 during bag-valve-mask 22 activation.

In the preferred embodiment of pharmacological introducing resuscitator attachment 10 it is contemplated for central housing 14, injection port 12, and nebulizer port 16 to be made as a one-piece unit of plastic materials, through molded construction. It is critical that resuscitator attachment 10, at a minimum, be made from materials which are chemically inert to the types of cardiac and asthma medications commonly required for administering to patients undergoing CPR in pre-hospital emergency situations.

To use the resuscitator attachment 10, pre-hospital emergency medical personnel (not shown) would first intubate a prone patient 26. With endo-tracheal tube 24 upwardly depending from the mouth of patient 26, bag-valve mask device 22 would be positioned over patient 26 with its air exhaust tube pointed in the direction of patient 26. When CPR is required for patient 26, airtight connection of the present invention between the air exhaust tube of bag-valve mask 22 and the upper portion of endo-tracheal tube 24, would be made to position injection port 12 and nebulizer port 16 so that they are each easily accessible should the administering of medications (not shown) by injection or nebulization into the lungs of patient 26 be required during CPR and for whom an intravenous line could not be established. Use of nebulizer port 16 and injection port 12 allow introduction of medications into patient 26 without interruption of CPR and eliminate the risk of dislodging endo-tracheal tube 24, the interruption of CPR formerly being required when the air exhaust tube of bag-valve mask device 22 was connected directly to endo-tracheal tube 24. After use on patient 26, it is contemplated for resuscitator attachment 10 to be disposable. Large end cap 32 could be removed from nebulizer port 16, as needed for use, then replaced on the distal end of nebulizer port 16 to provide an airtight connection for the continuation of CPR after medicine introduction into patient 26. Although not shown, bag-valve-mask 22 has at least one vent hole for the prevention of excess pressure build-up during CPR. As a result, the design of cap 32 is not required to accommodate excess pressures in order for it to accomplish its function of providing an air-tight seal. Elongated connecting member 36, if used, would retain large end cap 32 close at hand for prompt replacement of cap 32 on the distal end of nebulizer port 16 so that CPR need not be interrupted. In the alternative, it is within the scope of the present invention for cap 32 and the distal end of nebulizer port 16 to each comprise a nearly identical dimension to one of the openings in nebulizer 20 so that once nebulizer 20 is force-fit against the distal end of nebulizer port 16, open-ended nebulizer 20 could remain attached to nebulizer port 16, with cap 32 connected to and providing an air-tight seal for the open end of nebulizer 20. In this way repeat administering of nebulized medications (not shown) to patient 26 would require less procedural steps. It is contemplated for all caps 32 to be snap-on types of caps which are tight-fitting during use, but releasable with relative ease by emergency medical personnel (not shown).

What is claimed is:

1. An improved medication introducing device for connection between a bag-valve mask apparatus used for prehospital emergency respiratory assistance and the upper portion of an endo-tracheal tube in a patient undergoing CPR whose condition requires the administering of medications and in whom an intravenous line could not be established, said device comprising a central housing having an inside wall surface, an upper opening configured for airtight connection to the bag-valve mask apparatus, a lower opening configured for airtight connection to the endo-tracheal tube, at least one injection port for the administering of liquid medications through use of syringes, and at least one nebulizer port having a proximal end for administering medications in the form of a mist, said injection port and said nebulizer port laterally depending from said central housing and each having a hollow interior communicating with said lower opening so that medications can be administered to the patient without disconnection of the bag-valve mask apparatus and the concomitant interruption of CPR, and wherein the improvement comprises a deflecting barrier connected to said inside surface of said central housing adjacent to and above said proximal end.

2. The device of claim 1 further comprising said nebulizer port having a configuration with a reduced diameter on its proximal end and wherein said reduced diameter configuration is selected from a group consisting of two axial aligned and connected cylinders having different diameter dimensions; a truncated cone; a large cylinder joined to and axially aligned with a smaller truncated cone.

3. The device of claim 1 wherein said deflecting barrier is rigid, comprises a planar configuration, projects into said central housing, and is angled downwardly toward the patient.

4. The device of claim 1 wherein said deflecting barrier is rigid, comprises a planar configuration, projects into said central housing, is angled downwardly toward the patient, and comprises an end projection bent at an angle relative to the remainder of said barrier and oriented in a position approximately parallel to said inside surface of said central housing.

5. The device of claim 1 wherein said deflecting barrier is rigid, comprises an arcuate configuration, projects into said central housing, and depends downwardly toward the patient.

6. The device of claim 1 wherein said deflecting barrier comprises a flexible member which covers said proximal end during bag-valve mask activation, but which otherwise allows free flow of nebulized medication through said proximal end.

7. The device of claim 1 further comprising a plurality of end caps, one of said end caps being configured for airtight sealing of said nebulizer port and one of said caps for sealing said injection port.

8. The device of claim 7 wherein one of said end caps is a snap-fit type of cap configured for sealing said nebulizer port in an airtight and sufficiently secure manner to withstand the positive pressures generated by CPR.

9. The device of claim 8 wherein one of said end caps is two-sided, the first side of which is configured and dimensioned for connection to said nebulizer port, and the second side of which is configured and dimensioned for connection to one of the opposed open ends of a nebulizer tube used with said nebulizer port for the administering of medications in the form of a mist to a patient undergoing CPR.

10. The device of claim 1 wherein said central housing, said rigid barrier, said nebulizer port, and said injection port are made as a one-piece unit from molded construction.

11. An improved medication introducing device for connection between a bag-valve mask apparatus used for prehospital emergency respiratory assistance and the upper portion of an endo-tracheal tube in a patient undergoing CPR whose condition requires the administering of medications and in whom an intravenous line could not be established, said device comprising a central housing having an inside wall surface, an upper opening configured for airtight connection to the bag-valve mask apparatus, a lower opening configured for airtight connection to the endo-tracheal tube, at least one injection port for the administering of liquid medications through use of syringes, and at least one nebulizer port having a proximal end for administering medications in the form of a mist, said injection port and said nebulizer port laterally depending from said central housing and each having a hollow interior communicating with said lower opening so that medications can be administered to the patient without disconnection of the bag-valve mask apparatus and the concomitant interruption of CPR wherein the improvement comprises said nebulizer port having a configuration with a reduced diameter on its proximal end.

12. The device of claim 11 wherein said reduced diameter configuration is selected from a group consisting of two axial aligned and connected cylinders having different diameter dimensions; a truncated cone; a large cylinder joined to and axially aligned with a smaller truncated cone.

13. The device of claim 11 further comprising a deflecting barrier connected to said inside surface of said central housing adjacent to and above said proximal end.

14. The device of claim 11 wherein said deflecting barrier is rigid and is selected from a group consisting of a shielding member comprising a planar configuration which projects into said central housing and is angled downwardly toward the patient; a shielding member comprising a planar configuration which projects into said central housing, is angled downwardly toward the patient, and comprises an end projection that is bent at an angle relative to the remainder of said barrier and oriented in a position approximately parallel to said inside surface of said central housing; and a shielding member comprising an arcuate configuration which projects into said central housing and depends downwardly toward the patient.

15. The device of claim 11 wherein said deflecting barrier comprises a flexible shielding member which covers said proximal end during bag-valve mask activation, but which otherwise allows flow of nebulized medication through said proximal end.

16. The device of claim 11 further comprising a plurality of end caps, one of said end caps configured for airtight sealing of said nebulizer port and one of said caps for sealing said injection port.

17. The device of claim 16 wherein one of said end caps is a snap-fit type of cap configured for sealing said nebulizer port in an airtight and sufficiently secure manner to withstand the positive pressures generated by CPR.

18. The device of claim 17 wherein one of said end caps is two-sided, the first side of which is configured and dimensioned for connection to said nebulizer port, and the second side of which is configured and dimensioned for connection to an open end of said nebulizer tube.

19. A method for introducing both injected and nebulized medications into an endo-tracheal tube inserted into a patient undergoing pre-hospital emergency CPR without periodic interruption of said CPR, said method comprising the steps of providing a bag-valve type of mask, an endo-tracheal tube, a bag-valve mask resuscitator attachment having at least one capped injection port and one nebulizer port therethrough, a plurality of asthma medications, a nebulizer, a plurality of syringes pre-filled with cardiac medications, a two-sided easily releasable cap, and a patient requiring both CPR and medications;

placing said patient into a prone position;

inserting the lower end of said endo-tracheal tube into the mouth of said patient and securing said endo-tracheal tube within said patient;

connecting one side of said two-sided cap to said the distal end of said nebulizer port;

connecting said resuscitator attachment to the upper end of said endo-tracheal tube to form an airtight seal, and in a position where the proximal end of said injection port is adjacent to said endo-tracheal tube;

connecting the air exhaust tube of said bag-valve mask to the upper end of said resuscitator attachment to form an airtight seal;

when so indicated by the condition of said patient using one of said syringes to inject one of said cardiac medications through said injection port of said resuscitator attachment without interruption of CPR;

when so indicated by the condition of said patient removing said two-sided cap from said distal end of said nebulizer port, connecting said nebulizer to said distal end, and administering one of said asthma medications through said distal end without interruption of CPR; and re-installing said two-sided cap so that an air tight seal is once again established for the continuation of CPR and maximum delivery of nebulized medications through said endo-tracheal tube and into said patient.

20. The method of claim 19 wherein said step of re-installing said two-sided cap so that an air tight seal is once again established comprises the step of installing one of said sides of said cap to seal an open end of said nebulizer.

* * * * *